United States Patent [19]

Mancosu et al.

[11] Patent Number: 5,275,050
[45] Date of Patent: Jan. 4, 1994

[54] PROCESS FOR QUALITY CONTROL OF PRODUCTS HAVING PARTS MADE OF ELASTOMERIC MATERIAL

[75] Inventors: Federico Mancosu, Milan; Simone Schiatti, Desio, both of Italy

[73] Assignee: Pirelli Prodotti Diversificati S.p.A., Milan, Italy

[21] Appl. No.: 726,794

[22] Filed: Jul. 8, 1991

[30] Foreign Application Priority Data

Jul. 30, 1990 [IT] Italy .................. 21113 A/90

[51] Int. Cl.$^5$ .......................................... G01N 29/04
[52] U.S. Cl. ........................................ 73/587; 73/588; 73/801
[58] Field of Search ............... 73/587, 801, 588

[56] References Cited

U.S. PATENT DOCUMENTS

| | | | |
|---|---|---|---|
| 3,924,456 | 12/1975 | Vahaviolos | 73/587 |
| 3,946,600 | 3/1976 | Rettig et al. | 73/801 |
| 4,317,368 | 3/1982 | McElroy | 73/587 |
| 4,538,462 | 12/1985 | Hartog et al. | 73/801 |
| 4,549,437 | 10/1985 | Weins et al. | 73/587 |
| 4,700,577 | 10/1987 | Tripp | 73/801 |

FOREIGN PATENT DOCUMENTS

| | | | |
|---|---|---|---|
| 2155143 | 5/1973 | France | |
| 1392497 | 4/1988 | U.S.S.R. | 73/801 |
| 1452316 | 1/1990 | U.S.S.R. | 73/801 |

OTHER PUBLICATIONS

Ultrasonics, vol. 27, No. 3, May 1989, pp. 182–185; GB; F. Witos et al.: "Acoustic Emission Investigations of the . . .".

Primary Examiner—Hezron E. Williams
Assistant Examiner—Nashmiya Ashraf
Attorney, Agent, or Firm—Stevens, Davis, Miller & Mosher

[57] ABSTRACT

A flexible mounting (2) having a ring made of elastomeric material (3) fixedly engaged between an inner metal collar (4) and an outer metal collar (5) is mechanically stressed so that it undergoes a gradual elastic deformation corresponding to a relative displacement of 15 mm between the collars in a period of 20 seconds. Acoustic transducers (7) carry out the detection of the acoustic emissions occurring within the mounting itself and caused by structural instabilities arising in the flexible mounting while it is deformed. The acoustic transducers convert the acoustic emissions to electric signals that, after suitable amplification and discrimination, provide a reliable quality evaluation of the mounting being tested.

13 Claims, 3 Drawing Sheets

PROCESS FOR QUALITY CONTROL OF PRODUCTS HAVING PARTS MADE OF ELASTOMERIC MATERIAL

DESCRIPTION

The present invention relates to a process for quality control of products having parts made of elastomeric material.

More specifically, the process in reference is particularly designed to carry out non-distructive inspection tests on manufactured articles of finished products consisting of parts made of elastomeric material fixedly joined to parts made of stiffer material such as for example metal parts or reinforcement fibers, cords, fabrics.

For the sake of simplicity in the course of the present description reference will be particularly made, by way of example only, to the execution of tests on flexible mountings in motor vehicle engines.

However the process in question can be also used for the quality control of other kinds of products, such as for example driving belts, rubber pipes incorporating textile reinforcement structures, and others.

Presently, the quality control of manufactured articles or mechanical items having rubber parts joined to parts made of other materials, such as for example the flexible mountings for engines in motor vehicles is mostly based on the visual evaluation of the formation of crackings between the rubber parts and the metal parts when the mounting is submitted to a predetermined load.

In other words the operator designed to carry out the quality control submits the piece to be tested to the instantaneous action of an appropriate press and examines whether under a load generally equal to twice the maximum load foreseen under operating conditions, undesired separations between the edges of the elastomeric ring and metal collars do not occur.

In order to facilitate the visual inspection on both ends of the flexible mounting, a mirror is normally provided to be located under the mounting, which enables the operator to easily examine the behaviour of the elastomeric ring at the lower end thereof.

The above methods have several drawbacks as regards reliability.

First of all the efficiency of the quality control is subordinated to the attention paid by the operator during the execution of the test. In addition, possible irregularities on the piece to be tested can be evaluated and detected only when they occur at the outer surfaces of the piece which are directly visible.

On the contrary, irregularities taking place at the inside of the piece, at areas not visible by the operator, cannot be detected by means of the above described method.

From the foregoing it is apparent that it would be desirable to have at one's disposal methods and apparatus enabling a quality control on manufactured articles or finished products to be carried out in a very reliable manner without needing particular care by the operator for detecting, examining and signalling possible irregularities.

It is also necessary that the quality control be carried out within a very short lapse of time, immediately after the production of the articles to be submitted to tests, so as to be able to take timely measures when irregularities resulting from imperfect operation of the apparatus used in manufacturing said articles are found.

For the purpose, methods of quality control based on the so-called "acoustic emission" are known.

The acoustic emission is a physical phenomenon substantially consisting in releasing of energy pulses in the form of elastic waves from the inside of any material submitted to a mechanical or thermal stress.

The main causes of this pulse release can be substantially identified in the nucleation and growth of cracks and/or fractures, the generation and movement of molecular dislocations due to permanent deformation, the presence of impurities in the material, and other types of phenomena due to structure instability.

By applying suitable transducers, generally of the piezoelectric type, to the surfaces of pieces submitted to tests it is possible to convert said energy pulses generally named "events", to electric signals which can be processes in order to give data from which the operating behaviour of the inspected pieces can be deduced.

It is therefore apparent that methods based on the acoustic emission can be used for carrying out the quality control of mechanical items or manufactured articles of different types, by detecting the released energy pulses in the form of elastic waves at the formation or growth of structure defects when said mechanical items or manufactured articles are submitted to particular stresses.

However it is to be pointed out that the electric signals coming from the transducer or transducers are not only those caused by the above mentioned events.

In fact, signals from transducers are also affected by different noise sources of mechanical and/or electric origin. In principle, the mechanical noise sources comprise noises from the machines used in carrying out tests, noises present in the factory and so on. Electrical noise sources on the contrary are represented by the unavoidable electric noise connected with the use of apparatus designed to process the transducer signals, noises generated by electromagnetic interferences of various kind and so on.

Therefore it has been necessary to resort to particular expendients in order to distinguish signals caused by significant events occurring in the piece being tested from noise signals. In this connection transducers having a resonance frequency close to the typical frequency of elastic waves caused by events are selected so that most of the mechanical noises characterized by low frequencies and electric interferences characterized by high frequencies can be excluded.

In addition, signals coming from transducers and previously amplified are suitably filtered by threshold discriminators in order to eliminate pulses having an intensity lower than a predetermined value, commonly referred to as "threshold level".

In this way only significant events characterized by pulses of higher intensity than the threshold level are detected.

These significant events too are afterwards sorted out based on their length, in order to be sure that the final detection only takes place on events that have really occurred in the piece being examined.

However all expedients hitherto adopted in the field have permitted the execution of trustworthy quality tests only on manufactured articles or finished pieces made of rigid materials, such as for example metals, in which the elastic wave transmission is greatly facilitated.

On the contrary, all knowledges in the field have not yet allowed trustworthy quality controls to be carried out on manufactured articles or mechanical items such as for example the above mentioned flexible mountings containing parts made of elastomeric material in which the elastic wave transmission is greatly dampened.

It is apparent that if elastic waves are greatly dampened before they reach the transducers, it is very difficult to distinguish significant events for test purpose from noises and interferences of different origin.

The present invention aims at solving the problems of the known art and consequently providing a process enabling the execution of trustworthy quality tests by exploiting the acoustic emission phenomena in manufactured articles or metal items at least partly made of elastomeric material.

The above and further objects that will become more apparent in the course of the present description are substantially attained by a process for quality control of products having parts made of elastomeric material, characterized in that it comprises the following steps:

associating at least an acoustic transducer designed to convert elastic waves into electric signals, with a product;

submitting the product to elastic deformations gradually increasing in time;

detecting, by the acoustic transducer, the elastic waves occurring in the product during the gradual elastic deformation;

processing the electric signals coming from the transducer in order to obtain data relating to the behaviour of the product submitted to elastic deformation;

comparing the obtained data with previously input reference data in order to establish whether the behaviour of the product corresponds to the necessary quality requirements.

Further features and advantages will best be understood from the detailed description of a preferred embodiment of a process for quality control of products having parts made of elastomeric material in accordance with the invention, given hereinafter by way of non-limiting example with reference to the accompanying drawings, in which.

Figure 1:
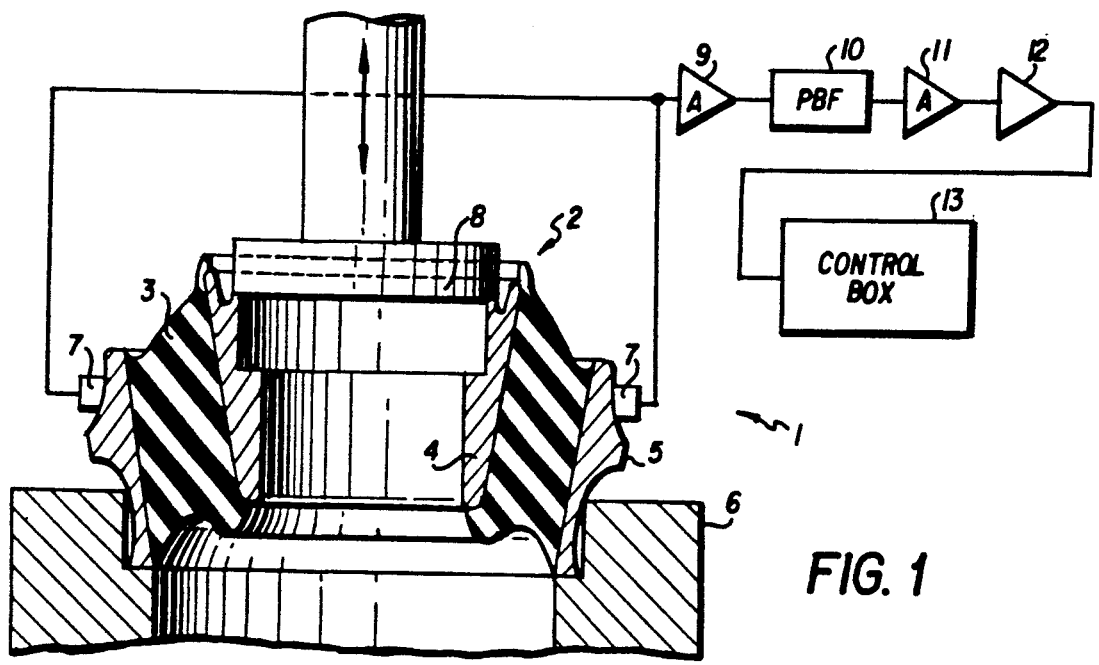
FIG. 1 is a diametrical sectional view of a flexible mounting for engines in motor vehicles, designed to be submitted to the quality test by an apparatus adapted for carrying out the process of the invention.
Figure 2:
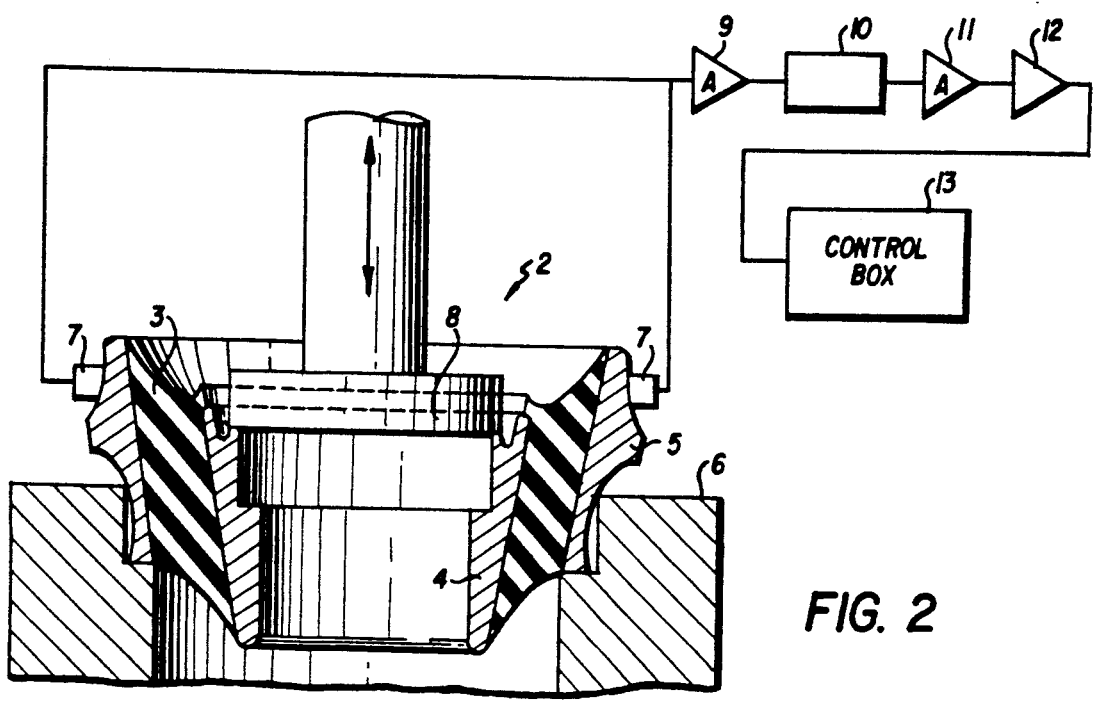
FIG. 2 shows the flexible mounting of FIG. 1 submitted to an elastic deformation of the ring made of elastomeric material.

Referring particularly to FIGS. 1 and 2, an apparatus for putting into practice the process in accordance with the present invention for quality control on products having parts made of elastomeric material has been generally identified by reference numeral 1.

In the example shown the product submitted to the test is represented, by way of example only, by a flexible mounting for motor vehicle engines generally identified by 2.

The flexible mounting 2 conventionally comprises an elastic ring made of elastomeric material 3 which is enclosed between an inner collar 4 and an outer collar 5 made of metal and disposed in coaxial relation with respect to each other.

The elastic ring 3 is firmly bonded to the inner and outer collars, 4 and 5, by a rubber-metal junction process. In known manner in a rubber-metal junction process at least a layer of adhesive material referred to as "cover" is first coated on the inner collar 4 and outer collar 5, on their surfaces designed to be brought into contact with the elastic ring 3; said cover consists of highly halogenated macromolecular substances such as 2,3-dichlorobutadiene-1.3-post-brominated polymers blended with high amounts of chlorinated rubber and high amounts of p-dinitrosobenzene.

The application of such an adhesive layer distributed in a liquid form, may be preceded by the application of a protective corrosion-resistant layer commonly referred to as "primer", containing modified phenolic resins in addition to substances similar to those previously described.

The primer, when drying is over, is fastened to the metal and the cover by a bond of physical nature.

Inner and outer collars 4 and 5 treated as described are housed in a mould into which elastomeric material in a raw state is injected for the formation of the elastic ring 3.

During the following vulcanization step that is achieved by heating the mould, a bond of chemical nature takes place between the elastomeric material and the adhesive layer or cover, giving rise to a stable junction between the elastic ring 3 and collars 4 and 5. The quality control test carried out by the process in reference aims at inspecting whether the adhesion between the elastomeric elastic ring 3 and collars 4 and 5 has occurred in a correct manner.

For the purpose, one or more acoustic transducers 7, preferably of the piezoelectric type and having a resonance frequency in the range of 100 to 300 KHz are associated with the flexible mounting 2 located in resting relationship on an annular support 6 acting on the outer collar 5. Said acoustic transducers 7 are designed to convert the elastic waves that will take place inside the mounting itself while the test is being executed, into electric signals.

Hereinafter by the expression "one or more transducers are associated with the flexible mounting" it is meant that the transducer can be applied to the mounting as shown in FIG. 1 or preferably applied to rigid parts of the test machine, among others for example the annular support 6 or thrust element 8.

Advantageously, the transducer or transducers 7 are provided to be applied to a distance lower than 3 cm from the point at which the acoustic emissions are supposed to have origin.

The application of transducers 7 conventionally takes place with the aid of suitable adhesive materials, also performing the function of interface between the mounting 2 and the transducers themselves.

In other solutions the transducer is fixedly and directly fastened to the machine by the metal parts.

When transducers 7 have been applied, mounting 2 is submitted to an elastic deformation step carried out by a thrust element 8 movable close to and away from the annular support element 6.

Advantageously, still in accordance with the present invention, the above elastic deformation gradually increases in time preferably at a rate comprised between 0.5 and 3 mm per second, and at all events not higher than 5 mm per second. Rates higher than the above values would make it difficult to distinguish the succession of the elastic wave emissions during the test.

Such a selected rate does not alter the test by introducing noise phenomena due to loads applied more or less instantaneously. Lower rates would not give rise to problems as regards the success of the test but they would involve a period of time that in some cases could be too long.

In the case of the flexible mounting as herein shown, the elastic deformation step is provided to take place, referring to FIGS. 1 and 2, by a 15 mm downwardly directed displacement of the inner collar 4 in a period of 20 seconds.

The displacement of the thrust element can be increasingly linear or follow an exponential or logarithmic law and the elastic deformation follows a law dependant on the shape of the piece being tested and the characteristics of the material.

While the elastic deformation is occurring, there is the detection, through the acoustic transducer or transducers 7, of the elastic waves resulting from energy pulses, hereinafter referred to as "events", released in the mounting structure 2 being tested due to small structure yieldings caused by the gradual growing of the load that gives rise to the deformation of the elastic ring 3.

The elastic deformation comes to an end before the load reaches the yield point value of the piece being tested.

The above elastic waves are picked up by transducers 7 that convert them to electric signals which can be suitably processed so as to deliver data relating to the behaviour of the mounting 2 submitted to test.

Figure 3:
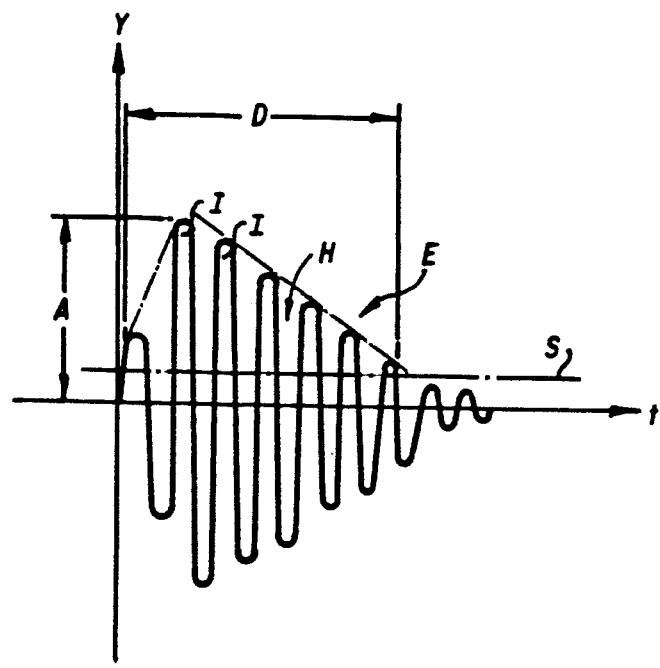
FIG. 3 is a diagram showing, by way of example, the growing in time of the electric pulses characterizing a typical event.

FIG. 3 graphically shows a typical event in the form in which it appears after the occurrence of phenomena connected with the propagation in the medium and interaction with the transducer.

As can be readily seen, the event, generally identified by "E", is formed with a periodical succession of electric pulses "I" the width "V" of which in the period of time "t" grows almost instantaneously and then progressively decreases.

In order that the electric pulses "I" may be considered an important part of event "E", they must have an intensity higher than a predetermined threshold level, represented by line "S".

The threshold level is comprised between 20 and 60 decibels and is normally in the range of 40 decibels.

The characteristic parameters of each event are represented by the width, denoted by "A", the number of pulses "I" exceeding the threshold level "S", the cyclic frequency of pulses "I", the duration "D" and the energy represented by the area identified at "H".

As can be viewed from FIG. 3, the width "A" is represented by the peak voltage "V" reached by pulses "I". The duration "D" is represented by the period of time "t" elapsing between the first and last pulses "I" passing through the threshold line "S".

The energy "H" is represented by the area subtended by the envelope of the rectified signal converted to a corresponding integer.

The processing of the electric signals emitted by transducers 7 first involves a pre-amplification of said signals through a preamplifier 9 with a gain of about 40 decibels. The amplified signals are filtered by a pass-band filter 10 tuned to the resonance frequency of transducers 7 that, in accordance with a preferred solution, corresponds to 150 KHz.

By suitably choosing the resonance frequency of the transducers and by adopting the pass-band filter 10 noise signals due for example to mechanical noises or electromagnetic interferences are advantageously eliminated.

After the first selection carried out by pass-band filters 10, the electric signals are submitted to a second amplification, with a gain adjustable through an amplifier 11, and are subsequently submitted to a second selection by means of a threshold discriminator 12.

The threshold discriminator 12 eliminates the electric signals of an intensity lower than the threshold level "S" in FIG. 3.

Signals beyond the threshold level "S" are sent to a control box 13 in which there is the elimination of events "E" which have a duration "D" higher or lower than a predetermined value varying depending upon the type of piece under examination. In the described case, the duration of events "E" is fixed to a value of 0.45 milliseconds.

An event-counting step is also carried out in the electronic control box 13 during which events "E" that have overcome the preceding three selections are counted; the count of the number of electric pulses "I" constituting the events themselves is also carried out, if necessary.

It is also possible to execute the measurement of the overall energy "H" of the events.

Data from the above counts will be compared with previously-input experimentally-obtained reference data in order to ascertain whether the mounting 2 under examination meets the necessary quality requirements or, on the contrary, must be discarded.

Said comparison step can be directly carried out by the electronic control box 13 in which the above mentioned reference data will have been stored.

Figure 4:
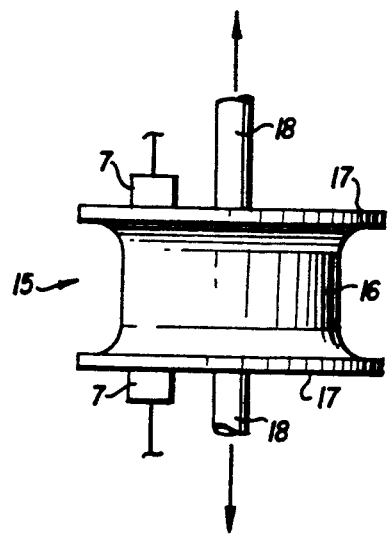
FIG. 4 is a diagrammatic side view of a test piece used for examining how the events detected by the process in reference vary depending upon different irregularities artificially produced in several test pieces identical to the one shown.

Graphics represented in FIGS. 5 to 8 show, depending upon time, the progressive detection of counts (pulses I drawn in FIG. 3) during several tests carried out in accordance with the process in question while submitting some test pieces of the type shown in FIG. 4 by reference numeral 15 to a pulling action at a deformation rate equal to 10 mm per minute as far as the crack point is reached.

As viewed from said figure, a test piece 15 is substantially comprised of a small block 16 of elastomeric material which has a diameter of 4 cm, a length of 25 mm and hardness of 65 Shore, the opposite ends of which are firmly linked by a rubber-metal junction process similar to the one previously described with reference to the flexible mounting 2, respective metal discs 17 of 6 cm in diameter and provided with gripping shanks 18 for connecting the test piece to an apparatus designed to carry out the pull test and not shown as of no importance to the ends of the invention.

Defects of different kind and importance have been willingly produced on some of the examined test pieces in order to evaluate how much the presence of a given defect affects the detection of the events during the test.

Figure 5:
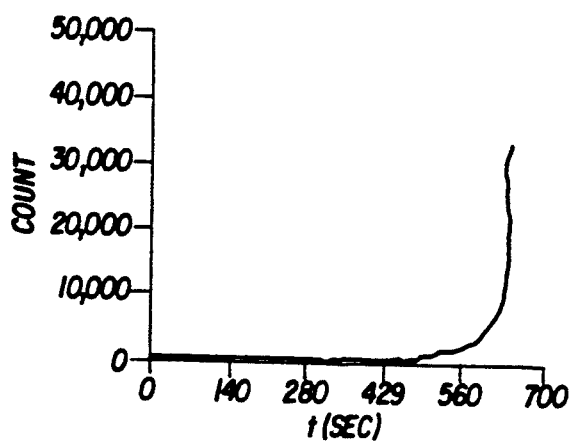
FIG. 5 is a diagram of the events detected during the elastic tensile stress deformation of a test piece according to FIG. 4, free of structure irregularities.

Graphic shown in FIG. 5 represents counts resulting from the examination of a test piece 15 free of defects.

As can be seen, value is practically zero until about 450 seconds from the beginning of the test. Then the sequence of counts progressively increases until fracture of the test piece occurs, after about 620 seconds.

Figure 6:
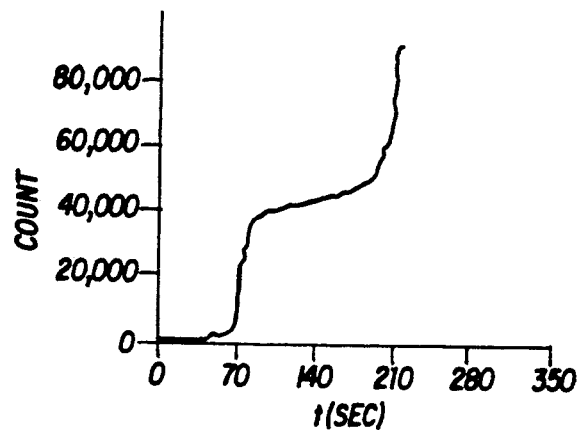
FIG. 6 is a diagram showing the events detected in a test piece identical to the one shown in FIG. 4 in which a defect at the rubber-metal junction, extending over 1.5 cm$^2$, has been artificially produced.

FIG. 6, on the contrary, shows the count diagram referred to a test piece 15 in which a non-attachment area extending over a surface of 1.5 cm$^2$ has been deliberately created on one of the attachment surfaces between the elastomeric small block 16 and the corresponding metal disc 17, by removing primer and cover layers before the rubber-metal junction.

As can be seen, the count value exhibits a sudden increase after only 70 seconds from the beginning of the test. Subsequently counts decrease according to a less marked amount until about 90 seconds, then the increase goes on in a marked manner as far as the test piece undergoes an ultimate yielding taking place 210 seconds after the beginning of test.

Figure 7:
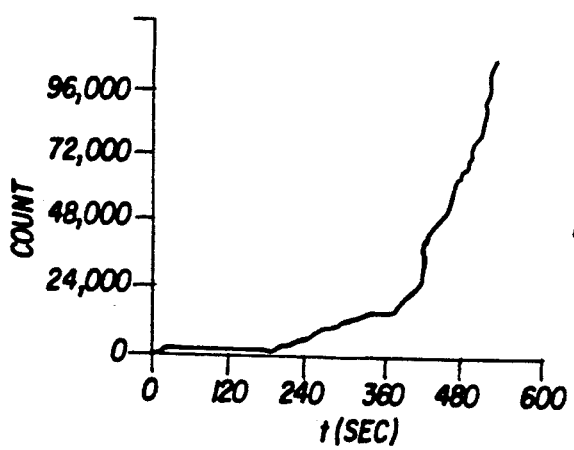
FIG. 7 shows the diagram of the events obtained on a test piece having a 0.25 cm$^2$ wide defect at the rubber-metal junction.

The graphic shown in FIG. 7 relates to a piece test 15 having a non-attachment area of 0.25 cm$^2$ over one of the mating surfaces between the small block 16 and respective metal disc 17.

In this case the count growth takes place more regularly and in a less marked manner than the case shown in FIG. 6, but at all events more quickly than in the case of the test piece 15 clear of defects described with reference to FIG. 5.

In greater detail the count growth begins after about 190 seconds and the test piece fracture occurs after 530 seconds from the beginning of test.

Figure 8:
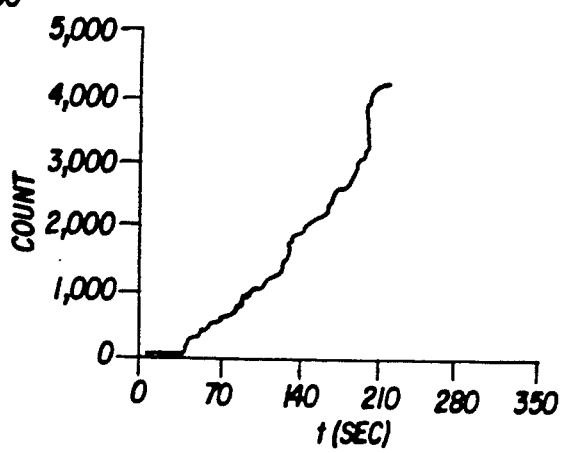
FIG. 8 is a diagram of the events occurred on a test piece in which the rubber-metal junction has been carried out in the absence of an adhesive.

Shown in FIG. 8 is the graphic relating to a test piece from one of the metal discs 17 of which the adhesive cover layer that would have offered the chemical bond with the elastomeric material of the small block 16 has been completely omitted.

The adhesion between the small block 16 and disc 17 therefore could only rely upon the primer layer offering a physical bond.

As can be seen, the count gradually increases in a substantially uniform manner after 30 seconds from the beginning of the test. The test piece fracture occurs after 210 seconds.

The foregoing proves that the process in reference is capable of giving trustworthy results since the analysis of counts takes place in an increasing manner proportionally to the importance of defects present on the test piece.

Many experimental tests carried out on flexible mountings of standard production have proved that many mountings which had already overcome the quality control test according to traditional methods, when a further test has been driven in accordance with the invention have revealed the presence of unacceptable defects.

In addition, it has been found that based on the development of the graphic of events it is also possible to go back to the type of defect present in the piece under examination.

The above description relating to the analysis carried out by observing counts is also valid as regards analysis on events.

It will be recognized that while the process in reference has been described referring particularly to the test made on flexible mountings, it can also be successfully carried out on mechanical members or manufactured articles of any kind.

For example, the process of the invention can be adopted for carrying out the quality control of driving belts formed, as known, from one or more layers of elastomeric material incorporating textile reinforcement cords.

Supposing a driving belt pulled along between two pulleys and using acoustic transducers applied to the pulleys or directly to the belt or mechanical parts of the test structure associated with the belt, it is in fact possible to detect events caused by fractures, dislodgements or detachment of the cords forming the textile reinforcement structure from the elastomeric layer.

The process can be adopted as well for the quality control of rubber pipes incorporating textile or metal reinforcement wires having a crossed flow.

In this case, the opposite ends of the pipe to be inspected are fixedly engaged in respective clamps and the acoustic transducers are applied either to the clamps or directly to the pipe.

Then air or other gas under pressure is blown into the pipe and it will tend to produce an elastic expansion of the pipe following which events caused by fractures, dislodgments or detachments from the reinforcement fibers of the elastomeric material are detected.

The present invention attains the intended purposes.

In fact the process in reference enables the obtention of a very reliable and quick quality control on any manufactured article or mechanical item in the structure of which at least a rubber part which can be welded to elements made of a different material is provided.

Obviously many modifications and variations can be made to the invention as conceived, all of them falling within the scope of the inventive idea characterizing it.

We claim:

1. A process for quality control of a product having a part made of elastomeric material bonded to parts made of stiffer materials, comprising the following steps:
    associating with at least one of the parts made of stiffer materials of said product at least an acoustic transducer having a resonance frequency in a range of 100 to 300 KHz, designed to convert elastic waves into electric signals;
    subjecting said elastomeric part to elastic deformations gradually increasing in time at a rate lower than 4 mm per minute;
    detecting, by the acoustic transducer, elastic waves occurring in said elastomeric part during the gradual elastic deformations;
    processing the electric signals coming from the acoustic transducer in order to obtain data relating to behavior of said elastomeric part as said elastomeric part is subjected to elastic deformations; and
    comparing the obtained data with experimentally obtained reference data previously input and stored in an electronic control box in order to establish whether undesired separation has occurred between the part made of elastomeric material and one of the parts made of stiffer material.

2. A process for quality control of a flexible mounting having an elastic ring made of elastomeric material fixedly fastened between an inner collar and an outer collar, comprising the following steps:

- associating at least one acoustic transducer having a resonance frequency in a range of 100 to 300 KHz, designed to convert elastic waves into electric signals, with the flexible mounting;
- submitting the flexible mounting to a stress to cause axial shifting of the inner collar relative to the outer collar in order to produce elastic deformations gradually increasing in time on the elastic ring at a rate lower than 4 mm per minute;
- detecting, by the acoustic transducer, elastic waves occurring in the mounting during the gradual elastic deformations;
- processing the electric signals coming from the acoustic transducer in order to obtain data relating to behavior of the mounting submitted to elastic deformations;
- comparing the obtained data with experimentally obtained reference data previously input and stored in an electronic control box in order to establish whether undesired separation has occurred between the elastic ring and either the inner collar or the outer collar.

3. A process according to claims 1, or 2, characterized in that said elastic deformations increase at a constant rate.

4. A process according to claims 1, or 2, characterized in that said elastic deformations constantly increase at a rate ranging between 0.5 and 3 mm per minute.

5. A process according to claims 1, characterized in that said elastic deformations are interrupted when the product is submitted to a load lower than its yield point.

6. A process according to claims 1, or 2, characterized in that said acoustic transducer is applied to a distance lower than 3 cm from an issue point of the elastic waves to be detected.

7. A process according to claims 1, or 2, characterized in that said electric signals comprise events ("E") consisting each of a number of electric pulses ("I"), the signal processing comprising the following steps:

- a first amplification of the electric pulses ("I");
- a first selection in order to eliminate electric pulses ("I") with frequencies which are different from a previously input frequency value;
- a second amplification of the electric pulses ("I"), the frequency of which corresponds to the previously input frequency value;
- a second selection in order to eliminate pulses ("I") of lower intensity than a previously input threshold level ("S");
- a third selection in order to eliminate events ("E") having a duration ("D") different from a previously input duration value;
- counting of the events ("E") of a duration ("D") corresponding to the previously input duration value.

8. A process according to claim 7, characterized in that said processing comprises a further count step for counting the electric pulses ("I") forming the events ("E") of a duration ("D") corresponding to the previously input duration value.

9. A process according to claim 7, characterized in that the first amplification takes place with a gain substantially corresponding to 40 decibels.

10. A process according to claim 7, characterized in that the previously input frequency value for the first selection is in the range of 100 KHz to 300 KHz.

11. A process according to claim 7, characterized in that the previously input frequency value for the first selection coincides with the resonance frequency value of the acoustic transducer, said transducer being of the piezoelectric type.

12. A process according to claim 7, characterized in that the previously input threshold level ("S") for the second selection is in the range of 20 decibels to 60 decibels.

13. A process according to claim 7, characterized in that the previously input duration value ("D") for the third selection substantially corresponds to 0.45 milliseconds.

* * * * *